US012714548B2

(12) United States Patent
Kramer

(10) Patent No.: US 12,714,548 B2
(45) Date of Patent: Aug. 25, 2026

(54) URETHRAL BARRIER DEVICE AND METHOD OF USE

(71) Applicant: Grace Kramer, Aberdeen, SD (US)

(72) Inventor: Grace Kramer, Aberdeen, SD (US)

( * ) Notice: Subject to any disclaimer, the term of this patent is extended or adjusted under 35 U.S.C. 154(b) by 332 days.

(21) Appl. No.: 18/539,889

(22) Filed: Dec. 14, 2023

(65) Prior Publication Data

US 2025/0195193 A1 Jun. 19, 2025

(51) Int. Cl.

| | |
|---|---|
| ***A61F 2/00*** | (2006.01) |
| ***A61F 13/472*** | (2006.01) |
| ***A61K 9/70*** | (2006.01) |
| *A61F 13/15* | (2006.01) |

(52) U.S. Cl.
CPC .......... *A61F 2/0009* (2013.01); *A61F 13/472* (2013.01); *A61K 9/7007* (2013.01); *A61F 2013/15048* (2013.01)

(58) Field of Classification Search
CPC .................. A61F 2/0009; A61F 13/472; A61F 2013/15048; A61K 9/7007
See application file for complete search history.

(56) References Cited

U.S. PATENT DOCUMENTS

| | | | | |
|---|---|---|---|---|
| 5,232,702 | A * | 8/1993 | Pfister | A61K 9/7069 424/443 |
| 5,908,379 | A | 6/1999 | Schaefer | |
| 8,889,655 | B2 | 11/2014 | London Brown | |
| 10,449,110 | B2 | 10/2019 | St. Anne | |
| 2010/0152687 | A1* | 6/2010 | Carlozzi | A61F 15/003 604/385.01 |
| 2013/0184778 | A1* | 7/2013 | St.Anne | A61F 15/002 607/2 |
| 2014/0024615 | A1* | 1/2014 | London Brown | A61P 31/04 514/55 |
| 2014/0221907 | A1* | 8/2014 | Scholz | A61F 13/00063 604/23 |
| 2017/0079832 | A1* | 3/2017 | Khun | A61F 13/472 |
| 2017/0281939 | A1* | 10/2017 | St. Anne | A61N 1/36014 |
| 2020/0261253 | A1* | 8/2020 | Moscherosch | A61F 13/82 |
| 2020/0352991 | A1* | 11/2020 | Modak | A61F 13/01017 |
| 2021/0361917 | A1 | 11/2021 | Edwards | |
| 2023/0301816 | A1* | 9/2023 | Sileika | C12N 1/20 |
| 2025/0107936 | A1* | 4/2025 | Loock | A61H 19/34 |

FOREIGN PATENT DOCUMENTS

| | | |
|---|---|---|
| CA | 2904917 | 3/2017 |
| DE | 102020129363 | 5/2022 |
| RU | 20042289337 | 12/2006 |

* cited by examiner

*Primary Examiner* — Ariana Zimbouski

(57) ABSTRACT

A urethral barrier device for preventing urinary tract infections includes a patch, which has a size and a shape allowing it to be positionable on a vestibule between labia minora and between a vaginal opening and a clitoris of a vulva. The patch thus overlays an external urethral orifice of a urethra without the patch impeding access to the vaginal opening or the clitoris. The patch comprises an upper layer and a lower layer. The upper layer comprises elastomer and thus is impervious to bacteria. The lower layer comprises adhesive and adhesively attaches the patch to the vestibule with the patch extending over the external urethral orifice. The patch prevents bacteria from entering the urethra through the external urethral orifice during sexual intercourse, thereby preventing a urinary tract infection.

2 Claims, 4 Drawing Sheets

URETHRAL BARRIER DEVICE AND METHOD OF USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to barrier devices and more particularly pertains to a new barrier device for preventing urinary tract infections (UTIs). UTIs are a common problem and cause significant morbidity and economic losses. UTIs prevention methods currently are limited to post-coital antibiotics.

(2) Description of Related Art Including Information Disclosed Under 37 CFR 1.97 and 1.98

The prior art relates to barrier devices. Prior art barrier devices intended to prevent urinary tract infections include gels that are applied over or injected into a urethra to form a temporary barrier. Finess® (Privy, Aliso Viejo, CA) is a urethral patch that is used to treat stress incontinence. Its use during sexual intercourse is not recommended as it may move, lose its adhesiveness, and not work properly. Related prior art comprises patches configured to be attachable over an anus of a user to limit potential for bacterial transfer to the urethra. Additional related prior art includes vaginal barrier devices, which form a barrier over the entirety of the vagina. Lady Patch® (ParaPatch, Inc, Los Angelas, CA) is a patch attachable to a clitoris to treat incontinence and does not form a urethral barrier. What is lacking in the prior art is a patch that is attachable over an external urethral orifice and which forms a urethral barrier that stays intact during sexual intercourse.

BRIEF SUMMARY OF THE INVENTION

An embodiment of the disclosure meets the needs presented above by generally comprising a patch, which has a size and a shape allowing the patch to be positionable on a vestibule between labia minora and between a vaginal opening and a clitoris of a vulva. The patch thus overlays an external urethral orifice of a urethra without the patch impeding access to the vaginal opening or the clitoris. The patch comprises an upper layer and a lower layer. The upper layer comprises elastomer and thus is impervious to bacteria. The lower layer comprises adhesive and is configured to adhesively attach the patch to the vestibule with the patch extending over the external urethral orifice. The patch is configured to prevent bacteria from entering the urethra through the external urethral orifice during sexual intercourse, thereby preventing a urinary tract infection.

Another embodiment of the disclosure includes a enables a method of preventing entry of microbes into a urethra during sexual intercourse. The method entails provision of a urethral barrier device, according to the disclosure above. Steps of the method include spreading the labia minora, positioning the patch between the labia minora and between a vaginal opening and a clitoris of the vulva, pressing the patch against the vestibule to attach the patch, engaging in sexual intercourse, and then removing and disposing of the patch.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
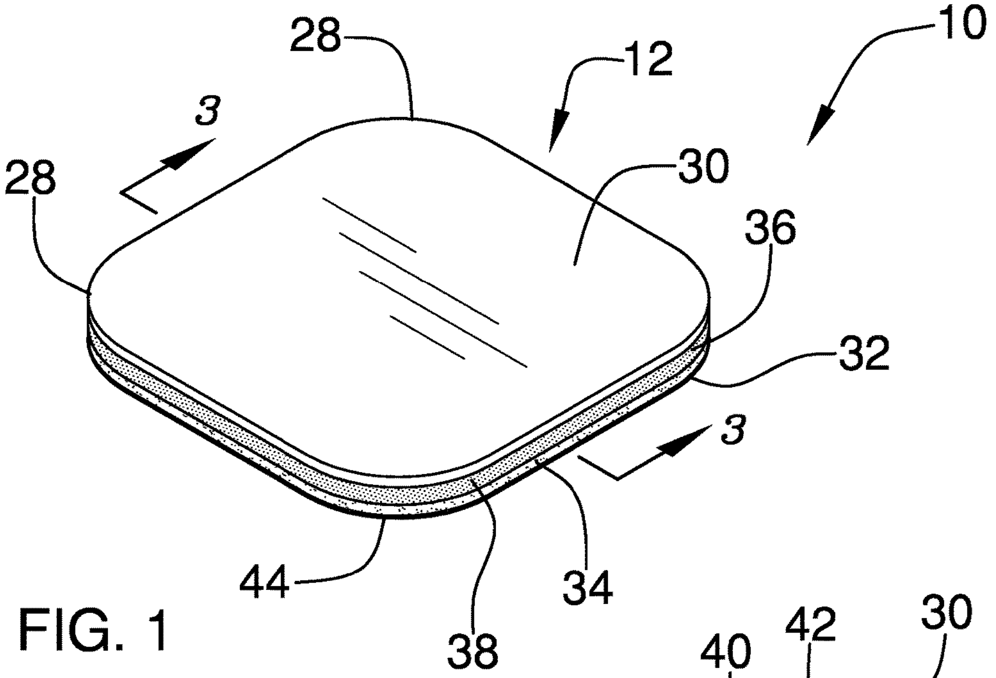
FIG. 1 is a top isometric perspective view of a urethral barrier device according to an embodiment of the disclosure.

With reference now to the drawings, and in particular to FIGS. 1 through 6 thereof, a new barrier device embodying the principles and concepts of an embodiment of the disclosure and generally designated by the reference numeral 10 will be described.

Figure 2:
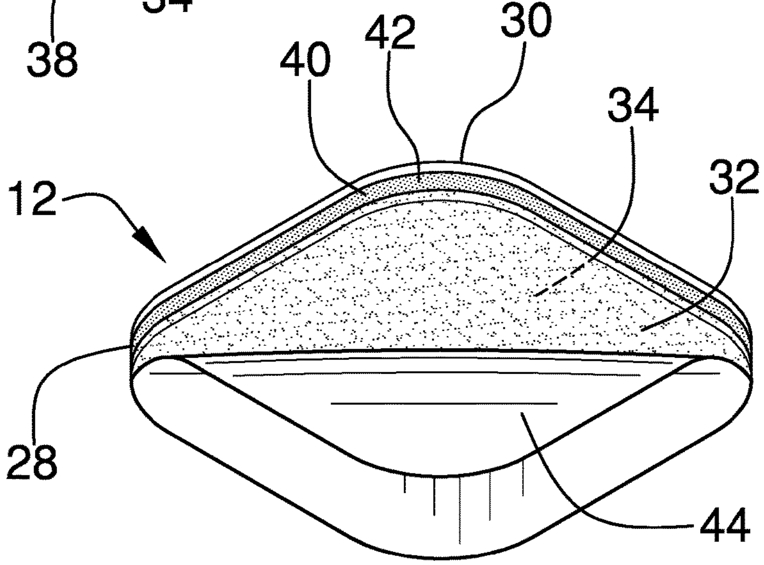
FIG. 2 is a bottom isometric perspective view of an embodiment of the disclosure.
Figure 3:
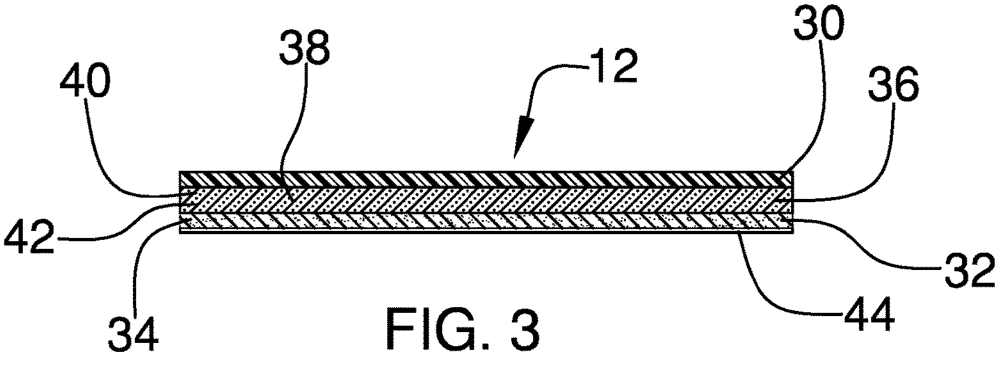
FIG. 3 is a cross-sectional view of an embodiment of the disclosure.
Figure 4:
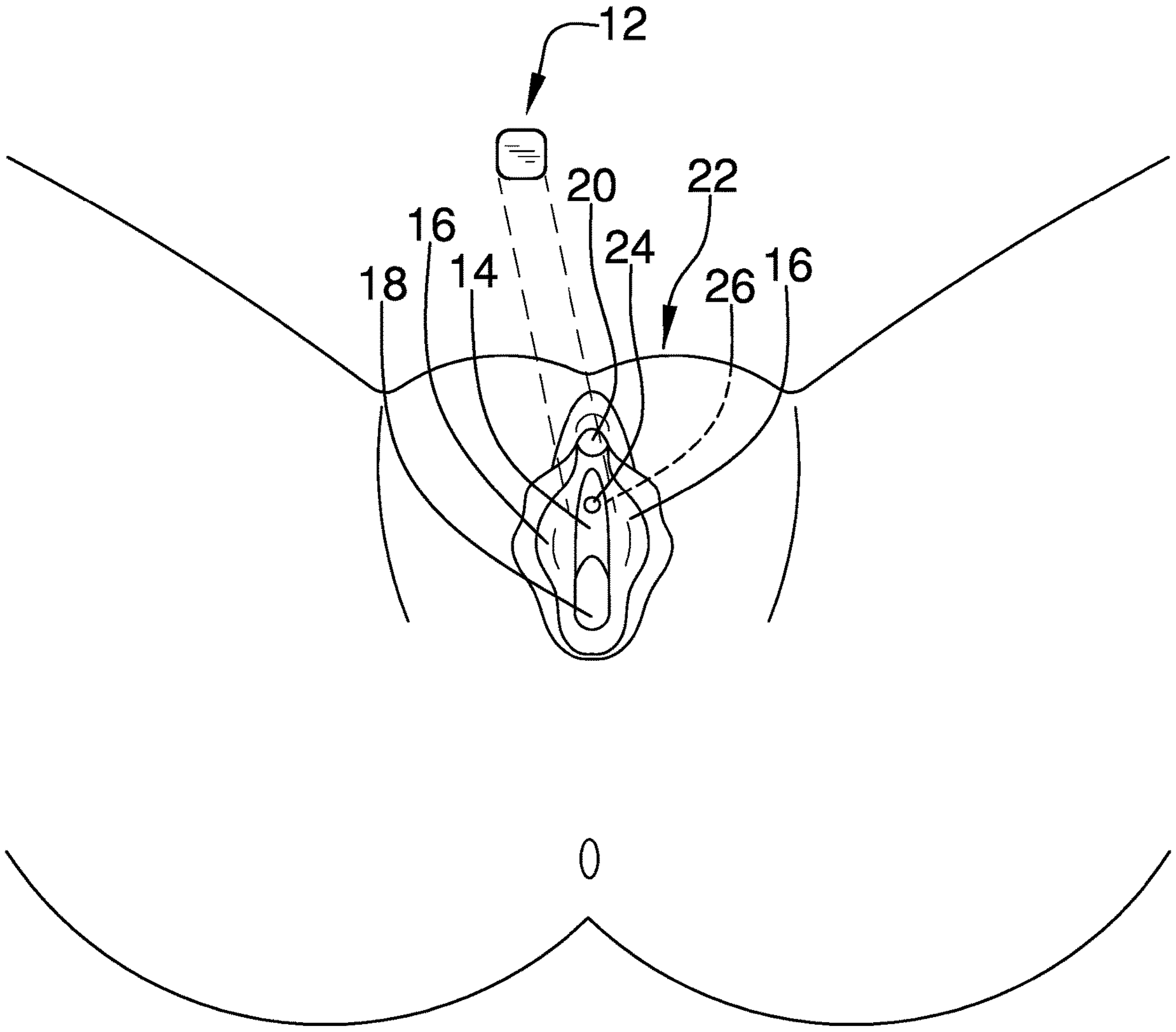
FIG. 4 is an in-use view of an embodiment of the disclosure.
Figure 5:
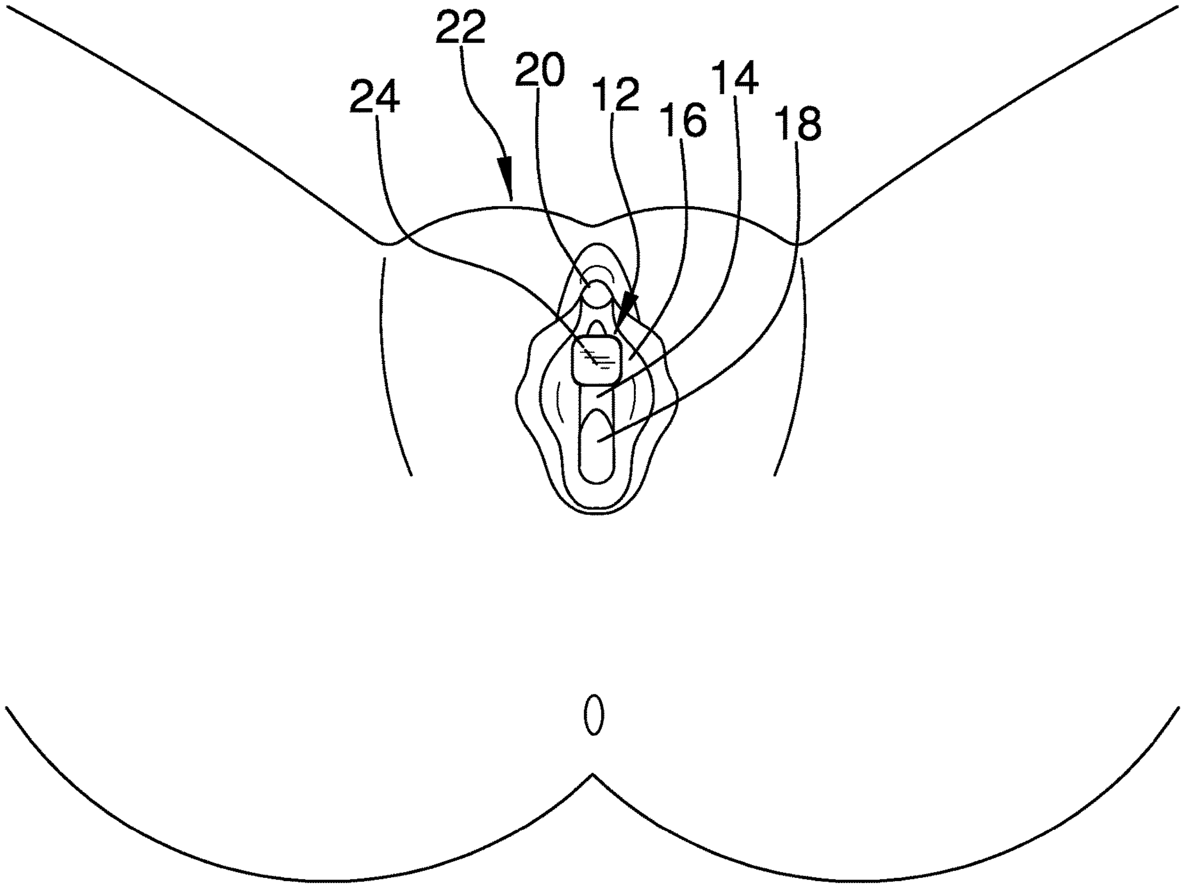
FIG. 5 is an in-use view of an embodiment of the disclosure.
Figure 6:
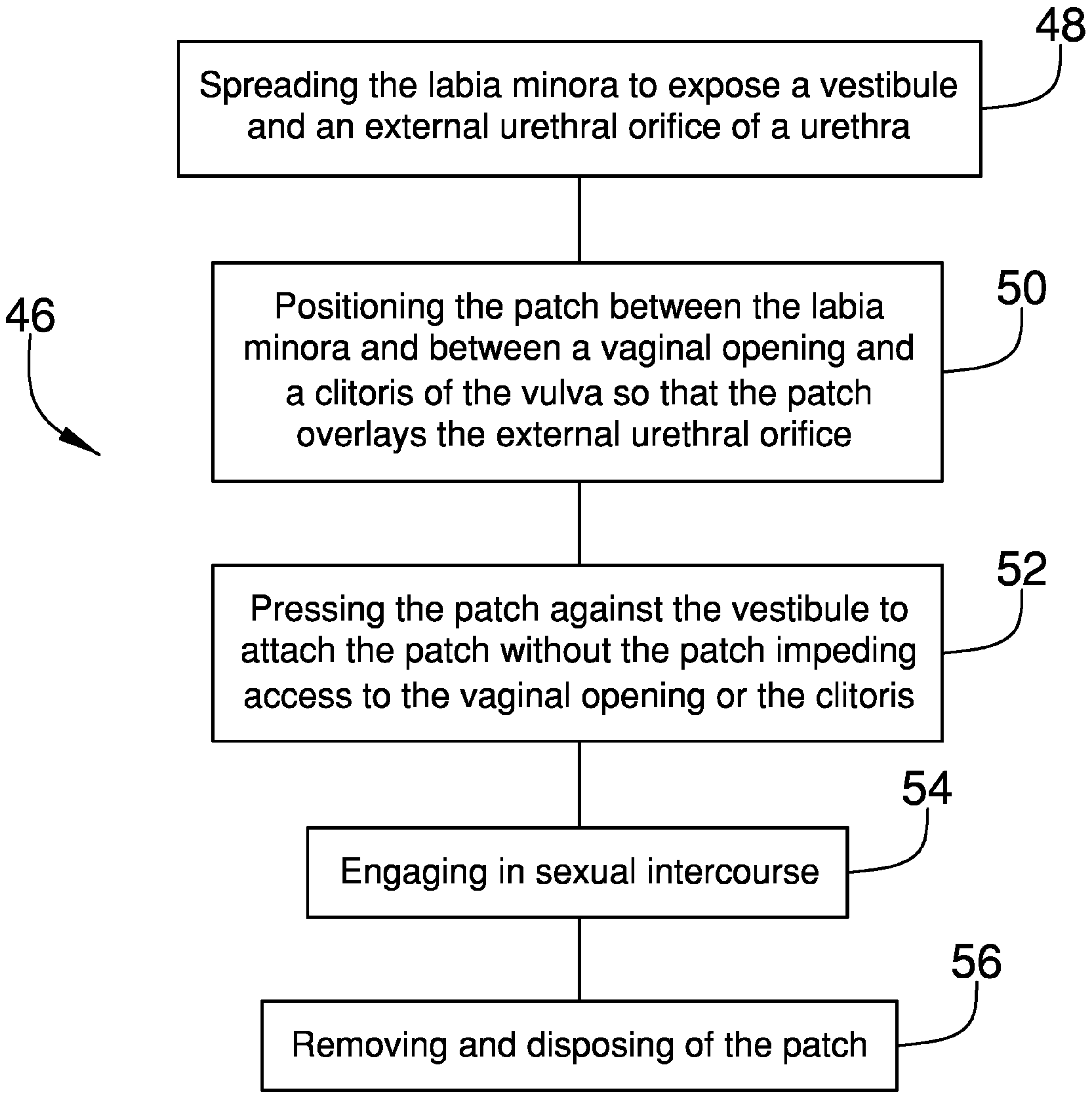
FIG. 6 is a flow diagram for a method utilizing an embodiment of the disclosure.

As best illustrated in FIGS. 1 through 6, the urethral barrier device 10 generally comprises a patch 12, which has a size and a shape allowing the patch 12 to be positionable on a vestibule 14 between labia minora 16 and between a vaginal opening 18 and a clitoris 20 of a vulva 22. The patch 12 thus overlays an external urethral orifice 24 of a urethra 26 without the patch 12 impeding access to the vaginal opening 18 or the clitoris 20. The shape of the patch 12 typically is substantially square, as is shown in FIGS. 1 and 2, wherein corners 28 of the patch 12 are convexly arcuate. Alternative shapes of the patch 12 also are anticipated by the present invention, such as, but not limited to, circular, ovoid, triangular, or the like. The size of the patch 12 is from 2.0 to 12.0 $cm^2$ and typically is from 4.0 to 10.0 $cm^2$. The patch 12 may be provided in a variety of sizes to complement vulva 22 of a variety of sizes. As will become apparent, the patch 12 being low profile and conformable to contours of the vulva 22 will render is less noticeable during sexual intercourse. The patch 12 also may be manufactured in a variety of colors so a respective color matching a skin tone of the user can be selected.

The patch 12 comprises an upper layer 30 and a lower layer 32. The upper layer 30 comprises elastomer and thus is impervious to bacteria. The upper layer 30 also may be substantially impermeable to water and comprise polyurethane, polyethylene, polypropylene, or the like. The lower layer 32 is coextensive with the upper layer 30 and comprises adhesive, such as a hydrogel adhesive 34, which are well known to those skilled in the art of adhesives for medical use. The lower layer 32 is configured to adhesively attach the patch 12 to the vestibule 14 with the patch 12 extending over the external urethral orifice 24. The patch 12 sealably closes the external urethral orifice 24 and thus is configured to prevent bacteria from entering the urethra 26 during sexual intercourse, thereby preventing or reducing risk of a urinary tract infection.

The patch 12 also may comprise a colloidal layer 36, which is sandwiched between the upper layer 30 and the lower layer 32. The colloidal layer 36 comprises a medicant 38, which is delivered through the lower layer 32 to one or both of the vestibule 14 and the urethra 26. The medicant 38 comprises one or more of a beneficial microorganism, an essential oil, a polyphenol, and a flavonoid. The medicant 38 may comprise witch-hazel extract 40. The medicant 38 may comprise one or more *lactobacillus* species 42 to inoculate the urethra 26 with the one or more *lactobacillus* species. The one or more *lactobacillus* species 42 typically are present as dehydrated granules in the colloidal layer 36.

As is shown in FIG. 2, a cover panel 44 is reversibly attached to the lower layer 32 to prevent inadvertent adhesion of the patch 12. The cover panel 44 is configured to be separated from the patch 12 to enable attachment of the patch 12 to the vestibule 14.

The urethral barrier device 10 enables a method of preventing entry of microbes into a urethra during sexual intercourse 46. The method 46 comprises providing the urethral barrier device 10, according to the specification above. A first step 48 of the method 46 is spreading labia minora 16 to expose a vestibule 14 of a vulva 22 and an external urethral orifice 24 of a urethra 26. A second step 50 of the method 46 is positioning the patch 12 between the labia minora 16 and between a vaginal opening 18 and a clitoris 20 of the vulva 22 so that the patch 12 overlays the external urethral orifice 24. A third step 52 of the method 46 is pressing the patch 12 against the vestibule 14 so that the adhesive attaches the patch 12 to the vestibule 14 without the patch 12 impeding access to the vaginal opening 18 or the clitoris 20. A fourth step 54 of the method 46 is engaging in sexual intercourse. A fifth step 56 of the method 46 is removing and disposing of the patch 12.

The method 46 also may entail provision of a sanitizing wipe (not shown) and a sterile gauze (not shown). The method 46 then would include a first preparatory step, prior to attachment of the patch 12, of wiping the vestibule 14 and the labia minora 16 with the sanitizing wipe. A second preparatory step would be drying the vestibule 14 and the labia minora 16 with the sterile gauze, at which point the patch 12 is attached to the vestibule 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A method of preventing entry of microbes into a urethra during sexual intercourse, the method comprising:

providing a patch having a size and a shape, the size and shape being such that the patch is positionable on a vestibule of the vulva between labia minora and between a vaginal opening and a clitoris of a vulva such that the patch overlays an external urethral orifice of the urethra and without the patch impeding access to the vaginal opening or the clitoris, the patch comprising an upper layer comprising elastomer such that the upper layer is impervious to bacteria; and a lower layer being coextensive with the upper layer and comprising adhesive, wherein the lower layer is configured for adhesively attaching the patch to the vestibule such that the patch extends over the external urethral orifice, wherein the patch is configured for preventing bacteria from entering the urethra through the external urethral orifice during sexual intercourse;

spreading the labia minora to expose the vestibule of the vulva and the external urethral orifice of the urethra, positioning the patch between the labia minora and between the vaginal opening and a clitoris of the vulva such that the patch overlays the external urethral orifice;

pressing the patch against the vestibule of the vulva so that the adhesive attaches the patch to the vestibule of the vulva without the patch impeding access to the vaginal opening or the clitoris;

engaging in sexual intercourse; and removing and disposing of the patch.

2. The method of claim 1, further including:

providing a sanitizing wipe and a sterile gauze; and the method including the following preparatory steps prior to attaching the patch to the vestibule:

wiping the vestibule and the labia minora with the sanitizing wipe; and drying the vestibule and the labia minora with the sterile gauze.

* * * * *